(12) United States Patent
Morley et al.

(10) Patent No.: US 7,914,522 B2
(45) Date of Patent: Mar. 29, 2011

(54) ROLL-PITCH-ROLL SURGICAL TOOL

(75) Inventors: Tracey A. Morley, Sunnyvale, CA (US); Daniel T. Wallace, Redwood City, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 0 days.

(21) Appl. No.: 11/968,813

(22) Filed: Jan. 3, 2008

(65) Prior Publication Data
US 2008/0103492 A1 May 1, 2008

Related U.S. Application Data

(60) Division of application No. 11/101,375, filed on Apr. 6, 2005, now Pat. No. 7,398,707, which is a continuation of application No. 10/752,934, filed on Jan. 6, 2004, now Pat. No. 6,902,560, which is a division of application No. 10/340,129, filed on Jan. 10, 2003, now Pat. No. 6,685,698, which is a division of application No. 09/626,527, filed on Jul. 27, 2000, now Pat. No. 6,746,443.

(51) Int. Cl.
*A61B 17/00* (2006.01)

(52) U.S. Cl. .......................................... 606/1; 74/490.06

(58) Field of Classification Search ........ 606/1; 901/29, 901/31, 130; 74/490.04, 490.06
See application file for complete search history.

(56) References Cited

U.S. PATENT DOCUMENTS

| | | | |
|---|---|---|---|
| 3,314,552 A | 4/1967 | Vertut | |
| 3,790,002 A * | 2/1974 | Germond et al. | 414/735 |
| 4,068,156 A | 1/1978 | Johnson et al. | |
| 4,370,091 A | 1/1983 | Gagliardi | |
| 4,606,695 A | 8/1986 | Lenz | |
| 4,626,165 A | 12/1986 | Nakashima et al. | |
| 4,685,349 A * | 8/1987 | Wada et al. | 74/490.04 |

(Continued)

OTHER PUBLICATIONS

Medical Robotics and Computer Assisted Surgery, Second Annual International Symposium, Nov. 4-7, 1995 at the Marriot Inner Harbor Hotel, Baltimore, Maryland, USA.

(Continued)

*Primary Examiner* — John Fox

(57) ABSTRACT

A robotic surgical tool includes an elongate shaft having a working end and a shaft axis, and a pair of linking arms each having a proximal end and a distal end. The proximal end is pivotally mounted on the working end of the shaft to rotate around a first pitch axis to produce rotation in first pitch. A wrist member has a proximal portion pivotally connected to the distal end of the linking arm to rotate around a second pitch axis to produce rotation in second pitch. An end effector is pivotally mounted on a distal portion of the wrist member to rotate around a wrist axis of the wrist member to produce rotation in distal roll. The wrist axis extends between the proximal portion and the distal portion of the wrist member. The elongate shaft is rotatable around the shaft axis to produce rotation in proximal roll. At about 90° pitch, the wrist axis is generally perpendicular to the shaft axis. The proximal roll around the shaft axis and the distal roll around the wrist axis do not overlap. The use of the linking arms allows the end effector to be bent back beyond 90° pitch. The ability to operate the end effector at about 90° pitch and to bend back the end effector renders the wrist mechanism more versatile and adaptable to accessing hard to reach locations, particularly with small entry points such as those involving spinal, neural, or rectal surgical sites.

9 Claims, 10 Drawing Sheets

U.S. PATENT DOCUMENTS

| | | |
|---|---|---|
| 4,762,455 A | 8/1988 | Coughlan et al. |
| 4,911,033 A | 3/1990 | Rosheim et al. |
| 4,913,617 A | 4/1990 | Nicholson |
| 5,036,724 A | 8/1991 | Rosheim |
| 5,078,140 A | 1/1992 | Kwoh |
| 5,178,032 A | 1/1993 | Zona et al. |
| 5,207,114 A * | 5/1993 | Salisbury et al. .......... 74/479.01 |
| 5,305,653 A | 4/1994 | Ohtani et al. |
| 5,524,180 A | 6/1996 | Wang et al. |
| 5,553,198 A | 9/1996 | Wang et al. |
| 5,697,256 A | 12/1997 | Matteo |
| 5,710,870 A | 1/1998 | Ohm |
| 5,754,741 A | 5/1998 | Wang et al. |
| 5,762,458 A | 6/1998 | Wang et al. |
| 5,792,135 A | 8/1998 | Madhani et al. |
| 5,797,900 A | 8/1998 | Madhani et al. |
| 5,808,665 A | 9/1998 | Green |
| 5,810,716 A | 9/1998 | Mukherjee et al. |
| 5,814,038 A | 9/1998 | Jensen et al. |
| 5,855,583 A | 1/1999 | Wang et al. |
| 5,907,664 A | 5/1999 | Wang et al. |
| 5,931,832 A | 8/1999 | Jensen |
| 5,934,148 A | 8/1999 | Haniya et al. |
| 6,132,441 A | 10/2000 | Grace |
| 6,197,017 B1 | 3/2001 | Brock et al. |
| 6,223,100 B1 | 4/2001 | Green |
| 6,786,896 B1 | 9/2004 | Madhani |
| 7,013,750 B1 | 3/2006 | Kazami |

OTHER PUBLICATIONS

Rosheim, "Robot Wrist Actuators", 1989, John Wiley & Sons, Inc., New York.

Vertut, Jean and Coeffet, Philippe Coiffet; "Robot Technology; vol. 3A Teleoperation And Robotics Evolution And Development"; 1986; Prentice-Hall, Inc; Englewood Cliffs, N.J.

* cited by examiner

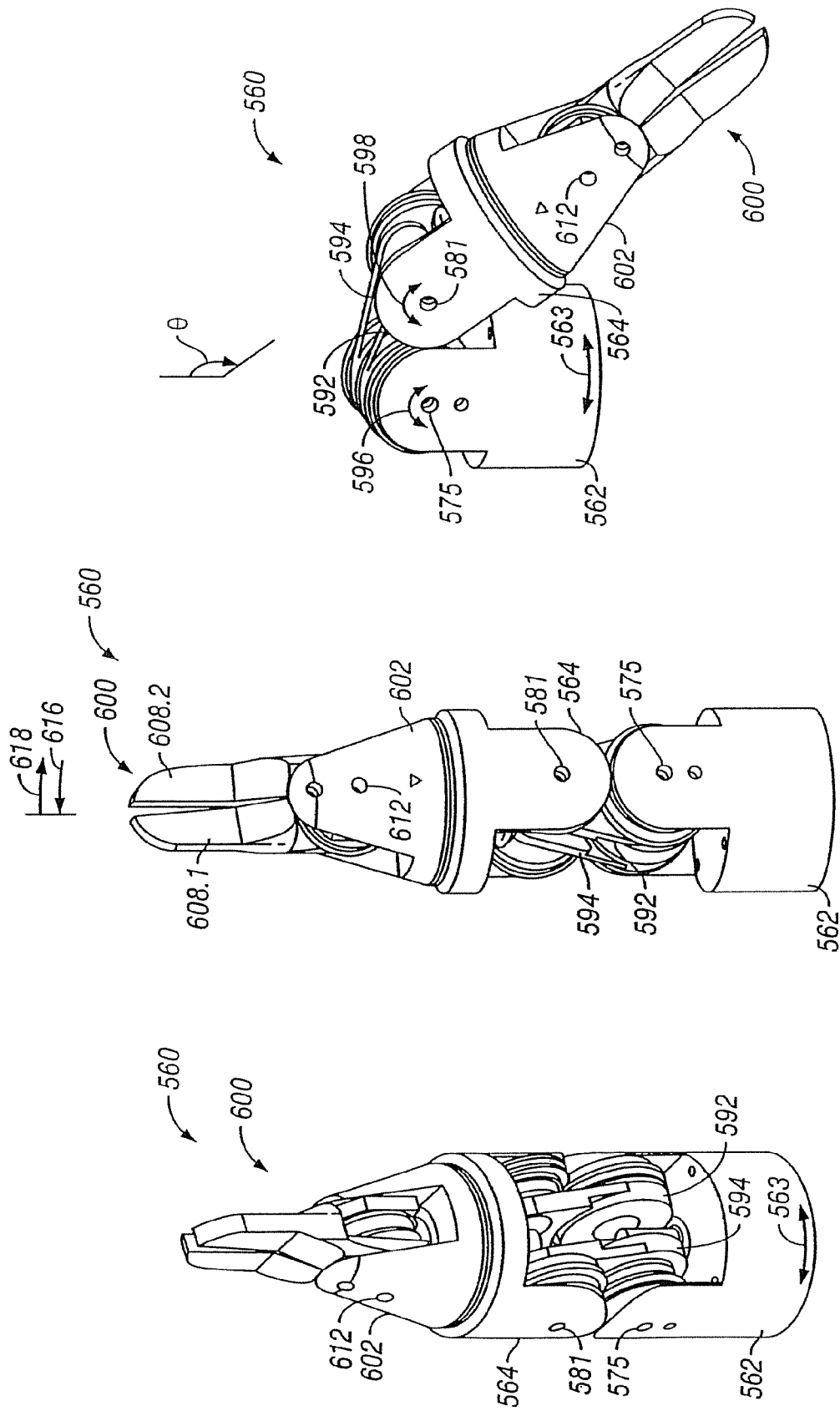

ROLL-PITCH-ROLL SURGICAL TOOL

CROSS-REFERENCES TO RELATED APPLICATIONS

This application is a division of U.S. patent application Ser. No. 11/101,375, filed Apr. 6, 2005; which is a continuation of U.S. patent application Ser. No. 10/752,934, filed Jan. 6, 2004, now U.S. Pat. No. 6,902,560; which is a division of U.S. application Ser. No. 10/340,129 filed Jan. 10, 2003, now U.S. Pat. No. 6,685,698; which is a division of Ser. No. 09/626,527, filed Jul. 27, 2000, now U.S. Pat. No. 6,746,443; the full disclosure of which is hereby incorporated by reference for all purposes.

This application is related to the following patents and patent applications, the full disclosures of which are incorporated herein by reference: PCT International Application No. PCT/US98/19508, entitled "Robotic Apparatus", filed on Sep. 18, 1998, U.S. application Ser. No. 09/418,726, entitled "Surgical Robotic Tools, Data Architecture, and Use", filed on Oct. 15, 1999; U.S. Application Ser. No. 60/111,711, entitled "Image Shifting for a Telerobotic System", filed on Dec. 8, 1998; U.S. application Ser. No. 09/378,173, entitled "Stereo Imaging System for Use in Telerobotic System", filed on Aug. 20, 1999; U.S. application Ser. No. 09/398,507, entitled "Master Having Redundant Degrees of Freedom", filed on Sep. 17, 1999, U.S. application Ser. No. 09/399,457, entitled "Cooperative Minimally Invasive Telesurgery System", filed on Sep. 17, 1999; U.S. application Ser. No. 09/373,678, entitled "Camera Referenced Control in a Minimally Invasive Surgical Apparatus", filed on Aug. 13, 1999; U.S. Provisional application Ser. No. 09/398,958, entitled "Surgical Tools for Use in Minimally Invasive Telesurgical Applications", filed on Sep. 17, 1999; and U.S. Pat. No. 5,808,665, entitled "Endoscopic Surgical Instrument and Method for Use", issued on Sep. 15, 1998.

BACKGROUND OF THE INVENTION

Advances in minimally invasive surgical technology could dramatically increase the number of surgeries performed in a minimally invasive manner. Minimally invasive medical techniques are aimed at reducing the amount of extraneous tissue that is damaged during diagnostic or surgical procedures, thereby reducing patient recovery time, discomfort, and deleterious side effects. The average length of a hospital stay for a standard surgery may also be shortened significantly using minimally invasive surgical techniques. Thus, an increased adoption of minimally invasive techniques could save millions of hospital days, and millions of dollars annually in hospital residency costs alone. Patient recovery times, patient discomfort, surgical side effects, and time away from work also be reduced with minimally invasive surgery.

The most common form of minimally invasive surgery may be endoscopy. Probably the most common form of endoscopy is laparoscopy, which is minimally invasive inspection and surgery inside the abdominal cavity. In standard laparoscopic surgery, a patient's abdomen is insufflated with gas, and cannula sleeves are passed through small (approximately ½ inch) incisions to provide entry ports for laparoscopic surgical instruments. The laparoscopic surgical instruments generally include a laparoscope (for viewing the surgical field) and working tools. The working tools are similar to those used in conventional (open) surgery, except that the working end or end effector of each tool is separated from its handle by an extension tube. As used herein, the term "end effector" means the actual working part of the surgical instrument and can include clamps, graspers, scissors, staplers, and needle holders, for example. To perform surgical procedures, the surgeon passes these working tools or instruments through the cannula sleeves to an internal surgical site and manipulates them from outside the abdomen. The surgeon monitors the procedure by means of a monitor that displays an image of the surgical site taken from the laparoscope. Similar endoscopic techniques are employed in, e.g., arthroscopy, retroperitoneoscopy, pelviscopy, nephroscopy, cystoscopy, cisternoscopy, sinoscopy, hysteroscopy, urethroscopy and the like.

There are many disadvantages relating to current minimally invasive surgical (MIS) technology. For example, existing MIS instruments deny the surgeon the flexibility of tool placement found in open surgery. Most current laparoscopic tools have rigid shafts, so that it can be difficult to approach the worksite through the small incision. Additionally, the length and construction of many endoscopic instruments reduces the surgeon's ability to feel forces exerted by tissues and organs on the end effector of the associated tool. The lack of dexterity and sensitivity of endoscopic tools is a major impediment to the expansion of minimally invasive surgery.

Minimally invasive telesurgical robotic systems are being developed to increase a surgeon's dexterity when working within an internal surgical site, as well as to allow a surgeon to operate on a patient from a remote location. In a telesurgery system, the surgeon is often provided with an image of the surgical site at a computer workstation. While viewing a three-dimensional image of the surgical site on a suitable viewer or display, the surgeon performs the surgical procedures on the patient by manipulating master input or control devices of the workstation. The master controls the motion of a servomechanically operated surgical instrument. During the surgical procedure, the telesurgical system can provide mechanical actuation and control of a variety of surgical instruments or tools having end effectors such as, e.g., tissue graspers, needle drivers, or the like, that perform various functions for the surgeon, e.g., holding or driving a needle, grasping a blood vessel, or dissecting tissue, or the like, in response to manipulation of the master control devices.

Some surgical tools employ a roll-pitch-yaw mechanism for providing three degrees of rotational movement to an end effector around three perpendicular axes. At about 90° pitch, the yaw and roll rotational movements overlap, resulting in the loss of one degree of rotational movement.

SUMMARY OF THE INVENTION

The present invention is generally directed to robotic surgery methods, devices, and systems. The invention provides a minimally invasive surgical tool which operates with three degrees of rotational movement at about 90° pitch. In particular, the surgical tool employs a roll-pitch-roll configuration in which an elongate shaft is rotatable in proximal roll, a wrist member is pivotally mounted on the working end of the elongate shaft to rotate in pitch, and an end effector is pivotally mounted on the wrist member to rotate in distal roll around the wrist axis of the wrist member. At about 90° pitch, the wrist axis is generally perpendicular to the shaft axis of the elongate shaft. The proximal roll around the shaft axis and the distal roll around the wrist axis do not overlap. In some embodiments, a pulley and cable mechanism is used to rotate and actuate the end effector.

In some embodiments, the end effector can be bent back beyond 90° pitch. The mechanism coupling the end effector to the working end of the elongate shaft allows the wrist member and end effector to bend back by an angle θ of more than about 90° from the forward position, desirably by more than about 120°, and more desirably by more than about 135°. The ability to operate the end effector at about 90° pitch and to bend back the end effector renders the wrist mechanism more versatile and adaptable to accessing hard to reach locations, particularly with small entry points such as those involving spinal, neural, or rectal surgical sites. In specific embodiments, a pair of linking arms are pivotally connected between the working end and the wrist member to facilitate bend back pitching while maintaining the size of the tool to a sufficiently small size for minimally invasive surgical applications.

In accordance to an aspect of the present invention, a minimally invasive surgical instrument comprises an elongate shaft having a working end and a shaft axis, and at least one linking arm having a proximal end and a distal end. The proximal end is pivotally mounted on the working end of the shaft to rotate around a first pitch axis which is nonparallel to the shaft axis. A wrist member has a proximal portion pivotally connected to the distal end of the linking arm to rotate around a second pitch axis which is nonparallel to the shaft axis. An end effector is pivotally mounted on a distal portion of the wrist member to rotate around a wrist axis of the wrist member. The wrist axis extends between the proximal portion and the distal portion of the wrist member. The elongate shaft is rotatable around the shaft axis.

In some embodiments, the first pitch axis and the second pitch axis are parallel, and are perpendicular to the shaft axis. A pair of linking arms are connected between the working end and the wrist member. The end effector includes an end effector support pivotally mounted on the distal portion of the wrist member to rotate around the wrist axis. The end effector includes at least one end effector link pivotally mounted on the end effector support to rotate around a pivot axis which is nonparallel to the wrist axis. The pivot axis may be perpendicular to the wrist axis. The end effector may include a pair of end effector links. The end effector links may be rotatable around the pivot axis to move toward and away from one another. The end effector links may be rotatable around the pivot axis to move together in the same direction. One of the end effector links may be fixed relative to the end effector support.

In accordance with another aspect of the invention, a minimally invasive surgical instrument comprises an elongate shaft having a working end and a proximal end. The elongate shaft has a shaft axis between the proximal end and the working end. A wrist member includes a wrist axis between a proximal portion and a distal portion. An end effector is pivotally mounted on the distal portion of the wrist member to rotate around the wrist axis. At least one linking member is rotatably coupled between the working end and the wrist member to permit rotation of the wrist member relative to the working end, from a forward position in which the wrist axis is oriented with the end effector at the distal portion pointing generally away from the proximal end of the elongate shaft, to a backward position in which the wrist axis is oriented with the end effector at the distal portion pointing generally toward the proximal end of the elongate shaft.

In accordance with another aspect of the present invention, a method of performing minimally invasive surgery in a body cavity of a patient comprises introducing an elongate shaft having a working end into the cavity. The elongate shaft has a proximal end and a shaft axis between the working end and the proximal end. A wrist member which is pivotally coupled with the working end is rotated relative to the working end. The wrist member having a wrist axis. The method further comprises rotating at least one of the elongate shaft around the shaft axis and an end effector pivotally mounted on the wrist member around the wrist axis to position the end effector at a desired location inside the cavity.

In some embodiments, the wrist member is rotated around a pitch axis which is perpendicular to at least one of the shaft axis and the wrist axis to change an angle between the wrist axis and the shaft axis. The wrist member is rotated relative to the working end until the wrist axis is approximately perpendicular to the shaft axis. The wrist member may be rotated relative to the working end from a forward position in which the wrist axis is oriented with the end effector pointing generally away from the proximal end of the elongate shaft, to a backward position in which the wrist axis is oriented with the end effector pointing generally toward the proximal end of the elongate shaft.

BRIEF DESCRIPTION OF THE DRAWINGS

FIG. 15 is another perspective view of the wrist mechanism of FIG. 13;

FIG. 16 is another perspective view of the wrist mechanism of FIG. 13; and

FIG. 17 is a perspective view of the Wrist mechanism of FIG. 13 schematically illustrating the bend back feature of the end effector.

DESCRIPTION OF THE PREFERRED EMBODIMENTS

Figure 1:
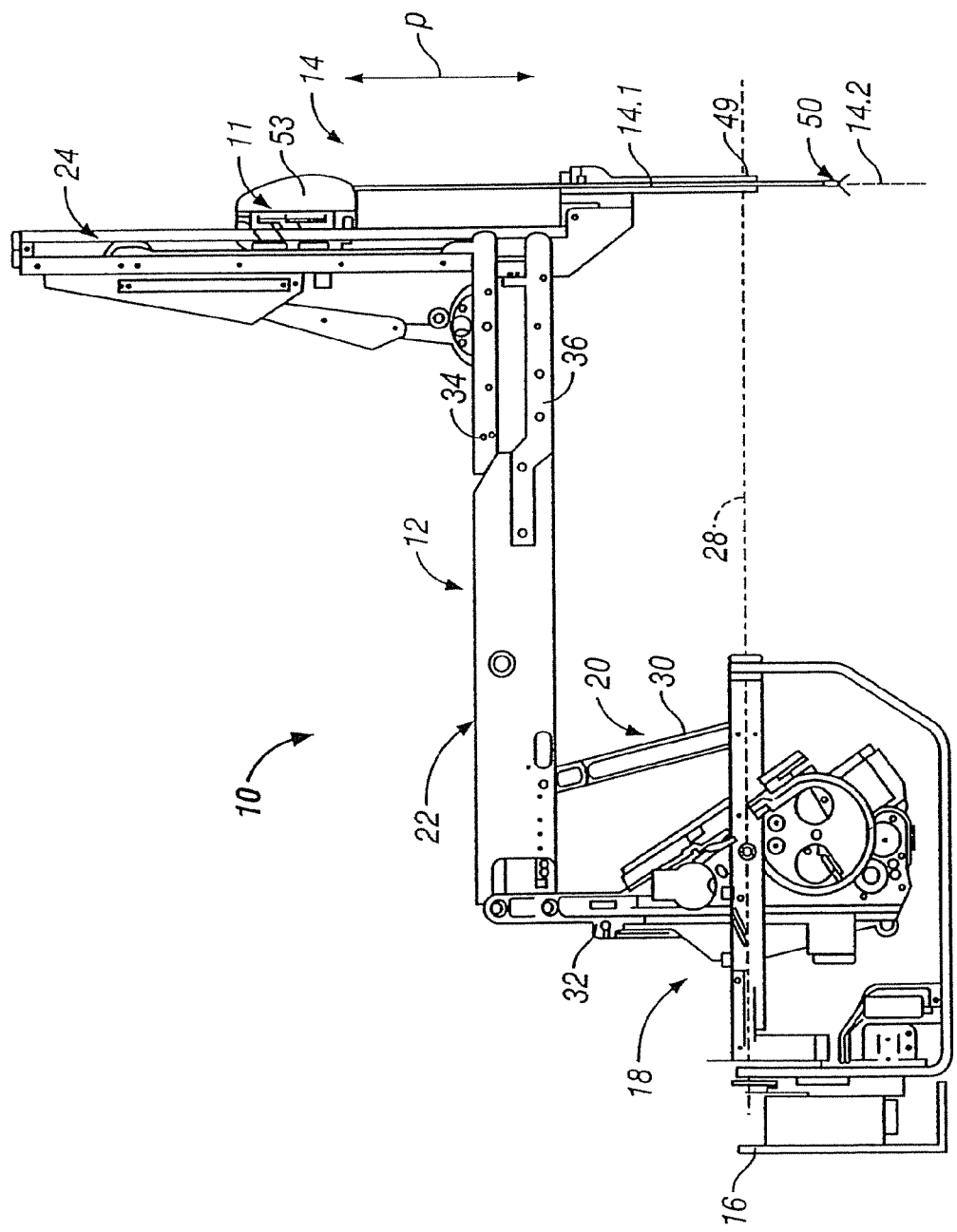
FIG. 1 is a side view of a robotic arm and surgical instrument assembly according to a preferred embodiment of the invention.
Figure 2:
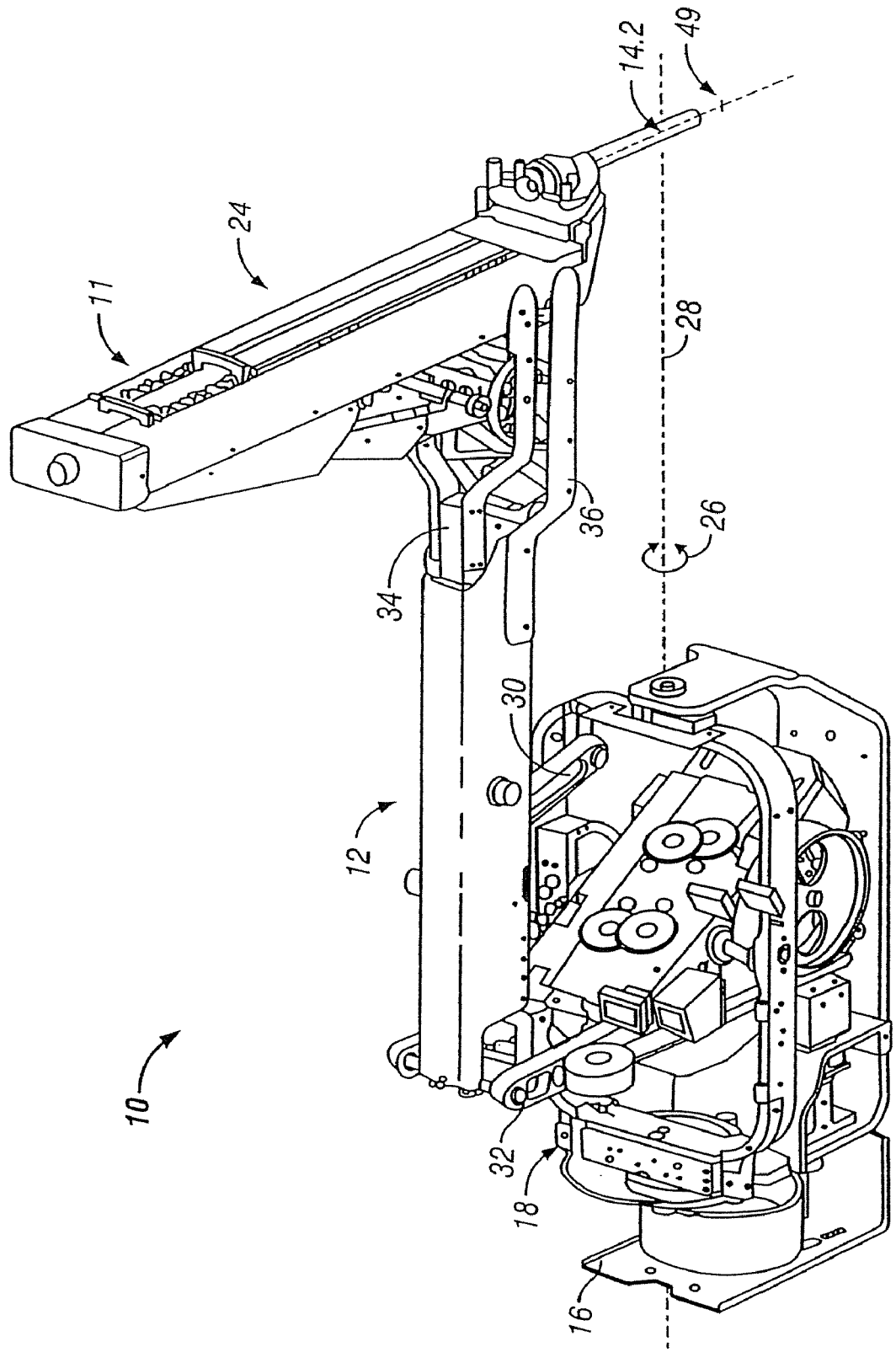
FIG. 2 is a perspective view of the robotic arm and surgical instrument assembly of FIG. 1.
Figure 3:
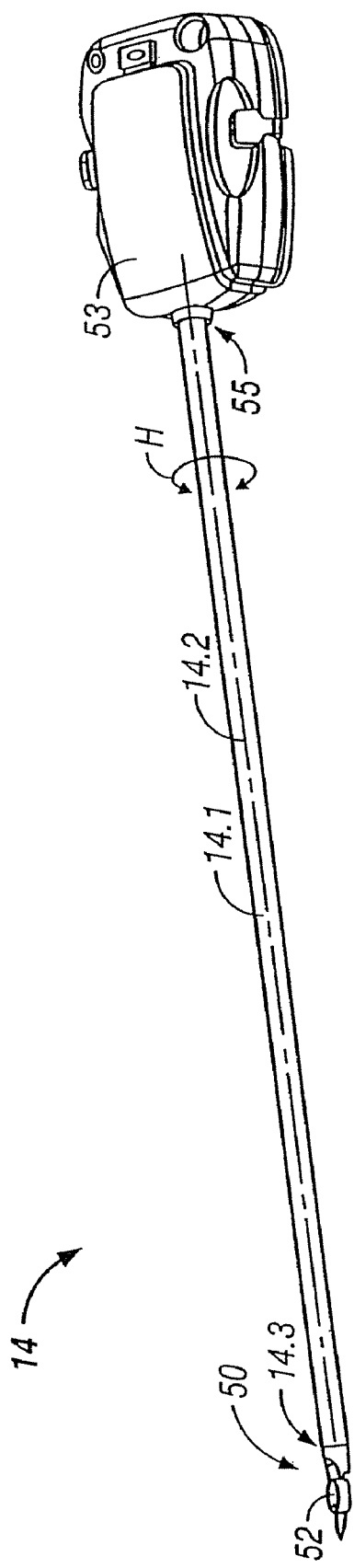
FIG. 3 is a perspective view of a surgical instrument according to a preferred embodiment of the invention.

FIGS. 1 and 2 illustrate a robotic arm and surgical instrument assembly 10. The assembly 10 includes a robotic arm 12 and a surgical instrument 14. FIG. 3 indicates the general appearance of the surgical instrument 14.

The surgical instrument 14 includes an elongate shaft 14.1. A wrist-like mechanism 50 is located at a working end of the shaft 14.1. A housing 53 arranged releasably to couple the instrument 14 to the robotic aim 12 is located at an opposed end of the shaft 14.1. In FIG. 1, and when the instrument 14 is coupled or mounted on the robotic arm 12, the shaft 14.1 extends along an axis indicated at 14.2. The instrument 14 is typically releasably mounted on a carriage 11 which is driven to translate along a linear guide formation 24 in the direction of arrows P. The surgical instrument 14 is described in greater detail herein below.

The robotic aim 12 is typically mounted on a base (not shown) by a bracket or mounting plate 16. The base is typically in the form of a mobile cart or trolley (not shown) which is retained in a stationary position during a surgical procedure.

The robotic arm 12 includes a cradle 18, an upper arm portion 20, a forearm portion 22, and the guide formation 24. The cradle 18 is pivotally mounted on the plate 16 in a gimbaled fashion to permit rocking movement of the cradle in the direction of arrows 26 about a pivot axis 28, as shown in FIG. 2. The upper arm portion 20 includes link members 30, 32 and the forearm portion 22 includes link members 34, 36. The link members 30, 32 are pivotally mounted on the cradle 18 and are pivotally connected to the link members 34, 36. The link members 34, 36 are pivotally connected to the guide formation 24. The pivotal connections between the link members 30, 32, 34, 36, the cradle 18, and the guide formation 24 are arranged to enable the robotic arm to move in a specific manner.

Figure 4:
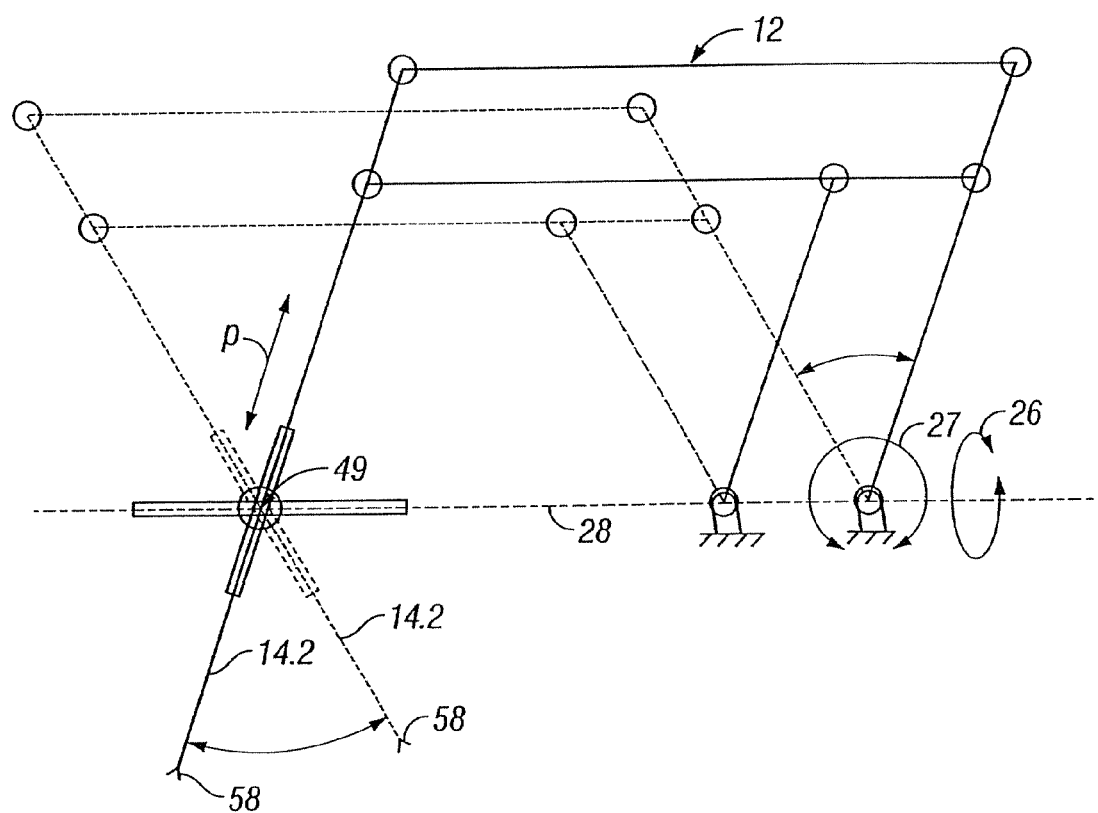
FIG. 4 is a schematic kinematic diagram corresponding to the side view of the robotic arm shown in FIG. 1, and indicates the arm having been displaced from one position into another position.

The movements of the robotic arm 12 is illustrated schematically in FIG. 4. The solid lines schematically indicate one position of the robotic arm and the dashed lines indicate another possible position into which the arm can be displaced from the position indicated in solid lines.

It will be understood that in a preferred embodiment, the axis 14.2 along which the shaft 14.1 of the instrument 14 extends when mounted on the robotic arm 12 pivots about a pivot center or fulcrum 49. Thus, irrespective of the movement of the robotic arm 12, the pivot center 49 normally remains in substantially the same position relative to the stationary cart 300 on which the arm 12 is mounted. In use, the pivot center 49 is typically positioned at a port of entry into a patient's body during an endoscopic procedure when an internal surgical procedure is to be performed. It will be appreciated that the shaft 14.1 extends through such a port of entry, the wrist-like mechanism 50 then being positioned inside the patient's body. Thus, the general position of the mechanism 50 relative to the surgical site in a patient's body can be changed by movement of the arm 12. Since the pivot center 49 is coincident with the port of entry, such movement of the arm does not excessively effect the surrounding tissue at the port of entry. It is to be appreciated that the field of application of the invention is not limited to surgical procedures at internal surgical sites only, but can be used on open surgical sites as well.

As can best be seen in FIG. 4, the robotic arm 12 provides three degrees of freedom of movement to the surgical instrument 14 when mounted thereon. These degrees of freedom of movement are firstly the gimbaled motion indicated by arrows 26, pivoting or pitching movement as indicated by arrows 27, and the linear displacement in the direction of arrows P. Movement of the arm as indicated by arrows 26, 27 and P is controlled by appropriately positioned actuators, e.g., electrical motors or the like, which respond to inputs from its associated master control to drive the arm 12 to a desired position as dictated by movement of the master control.

Roll-Pitch-Yaw Mechanism

Figure 7:
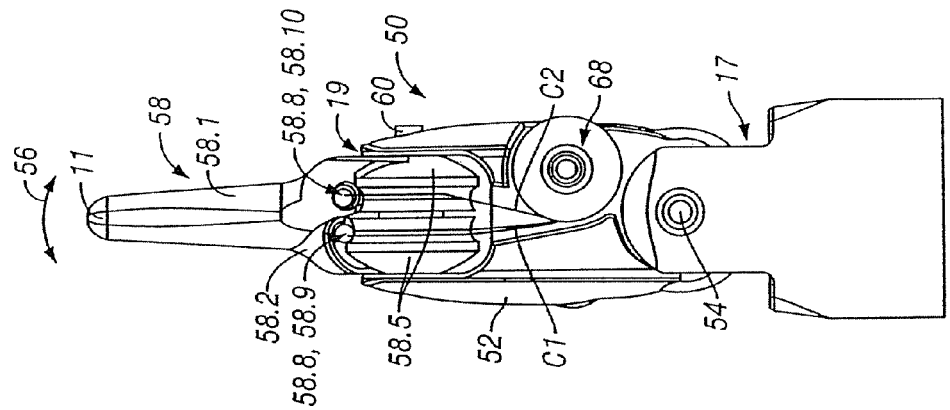
FIG. 7 is a side view of the wrist mechanism of FIG. 5 along arrow VII.
Figure 6:
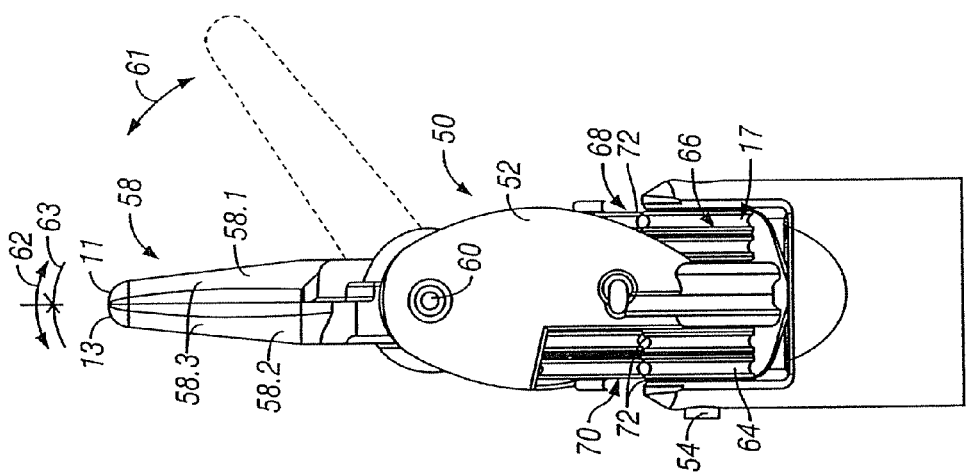
FIG. 6 is a front view of the wrist mechanism of FIG. 5 along arrow VI.
Figure 5:
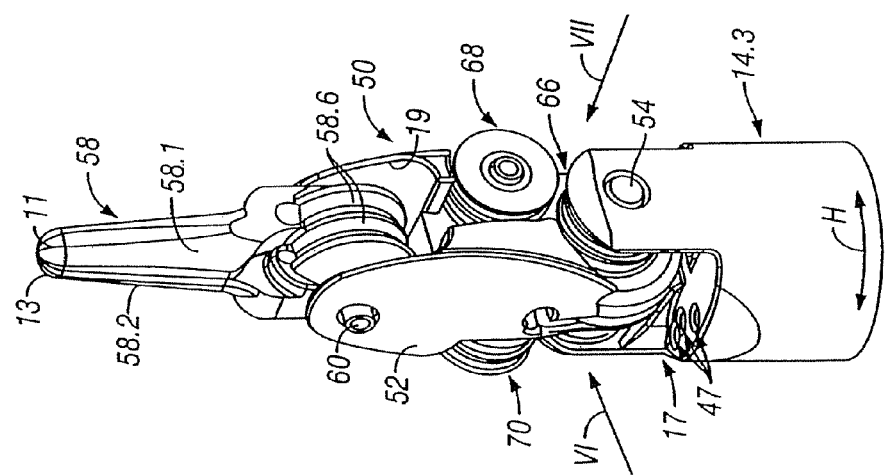
FIG. 5 is a perspective view of a roll-pitch-yaw wrist mechanism.

FIGS. 5, 6 and 7 show a roll-pitch-yaw wrist-like mechanism 50. In FIG. 5, the working end of the shaft 14.1 is indicated at 14.3. The wrist-like mechanism 50 includes a rigid wrist member 52. One end portion of the wrist member 52 is pivotally mounted in a clevis 17 on the end 14.3 of the shaft 14.1 by means of a pivotal connection 54. As best seen in FIG. 7, the wrist member 52 can pitch in the direction of arrows 56 about the pivotal connection 54. This rotation around the pivotal connection 54 in the direction 56 is referred to as the pivot or pitch of the wrist member 52. The end 14.3 is rotatable with the shaft 14.1 around the axis 14.2 in the direction H, as shown in FIGS. 3 and 5. This rotation around the axis 14.2 in the direction H is referred to as the roll of the working end 14.3.

An end effector, generally indicated by reference numeral 58, is pivotally mounted on an opposed end of the wrist member 52. The end effector 58 is in the form of forceps or graspers for grasping tissue or the like during a surgical procedure. Accordingly, the end effector 58 has two parts 58.1, 58.2 together defining a jaw-like arrangement. The end effector 58 is pivotally mounted in a clevis 19 on an opposed end of the wrist member 52, by means of a pivotal connection 60. Free ends 11, 13 of the parts 58.1, 58.2 are angularly displaceable about the pivotal connection 60 toward and away from each other as indicated by arrows 62, 63 in FIG. 6. This movement of the parts 58.1, 58.2 is referred to as the grip of the end effector 58. The members 58.1, 58.2 can be displaced angularly about the pivotal connection 60 to change the orientation of the end effector 58 as a whole, relative to the wrist member 52. Thus, each part 58.1, 58.2 is angularly displaceable about the pivotal connection 60 independently of the other, so that the end effector 58 is, as a whole, angularly displaceable about the pivotal connection 60 in the direction 61, as indicated in dashed lines in FIG. 6. This rotation around the pivotal connection 60 in the direction 61 is referred to the yaw of the end effector 58. The wrist mechanism 50 as illustrated in FIGS. 5-7 is referred to as a roll-pitch-yaw mechanism having roll in the direction H, pitch in the direction 56, and yaw in the direction 61.

The parts 58.1, 58.2 each include an elongate finger portion or end effector element 58.3 and an end effector mounting formation in the form of, e.g., a pulley portion 58.5. In a preferred embodiment, the finger portion 58.3 is integrally formed with the pulley portion 58.5. The pulley portion 58.5 defines a circumferentially extending channel 58.6 in which an elongate element in the form of, e.g., an activation cable, is carried. A generally circumferentially directed hole 58.8 extends through a nape region of the finger portion 58.3 and generally in register with the circumferentially extending channel 58.6. The hole 58.8 has a first portion 58.9 and a second portion 58.10 having a diameter greater than the first portion 58.9. In use, the activation cable has a thickened portion along its length which seats in the hole portion 58.10, the rest of the activation cable then extending along the channel 58.6 in opposed directions. The thickened portion is crimped in its seated position in the hole portion 58.10 so as to anchor the cable in the hole 58.8. It will be appreciated that a greater force is necessary to clamp the free ends together when gripping an object therebetween, than that which is required to open the free ends 11, 13. Thus, the thickened portion of the cable is urged against an annular stepped surface between the hole portion 58.9 and the hole portion 58.10, when the free ends 11, 13 are urged into a closed condition.

As best seen in FIG. 6, the wrist member 52 is flanked by two sets of pulleys 64, 66 which are coaxially positioned on the pivotal connection 54 and in the clevis 17 at the end 14.3 of the shaft 14.1. Two further sets of pulleys 68, 70 are rotatably mounted on opposed sides of the wrist member 52. Each pulley of the set of pulleys 68 on the one side of the wrist member 52 is generally co-planar with an associated pulley of the pulley set 66. Furthermore, each of the pulleys 68 is positioned such that its circumference is in close proximity to the circumference of its associated pulley of the pulley set 66. A similar arrangement exists for each pulley of the pulley set 70 on the other side of the wrist member and its associated pulley of the pulley set 64. Thus, the circumferentially extending channel formation of each pulley of the pulley sets 68, 70 and their associated pulleys of the pulley sets 64, 66 define between each of them a space 72 through which an activation cable can snugly pass.

A plurality of elongate elements, e.g., cables, are used to effect movement of the wrist mechanism 50 and end effector 58. As seen in FIG. 7, two cables C1, C2 are anchored on the parts 58.1, 58.2, respectively, to effect movement of the parts 58.1, 58.2 independently in directions 62, 63 or as a whole (FIG. 6).

Cable C1 rides over an outer pulley of the pulley set 64, an outer pulley of the pulley set 70, over part of circumferential channel 58.6 of the pulley portion 58.5 of the part 58.2 of the end effector 58, through the hole 58.8, again along part of the circumferential channel 58.6 of the pulley portion 58.5, over an outer pulley of the pulley set 68 and over an outer pulley of the pulley set 66. Similarly, cable C2 rides over an inner pulley of the pulley set 64, over an inner pulley of the pulley set 70, along the circumferential channel 58.6 of the part 58.1 of the end effector 58, through the hole 58.8 of the part 58.1, again along the circumferential channel 58.6 of the pulley portion 58.5, over an inner pulley of the pulley set 68 and over an inner pulley of the pulley set 66. The cables C1, C2 pass from the wrist mechanism 50 through appropriately positioned holes 47 in the base region of the clevis 17 (FIG. 5), and internally along the shaft, toward the housing 53 (FIG. 3). The housing 53 includes driving members, e.g., in the form of spool assemblies for manipulating the cables. Additional details of the spool assemblies and the grip mechanism for manipulating the finger portions 58.1, 58.2 to achieve gripping as well as description of various surgical tools can be found in U.S. application Ser. No. 09/398,958, entitled "Surgical Tools for Use in Minimally Invasive Telesurgical Applications", filed on Sep. 17, 1999.

Figure 8:
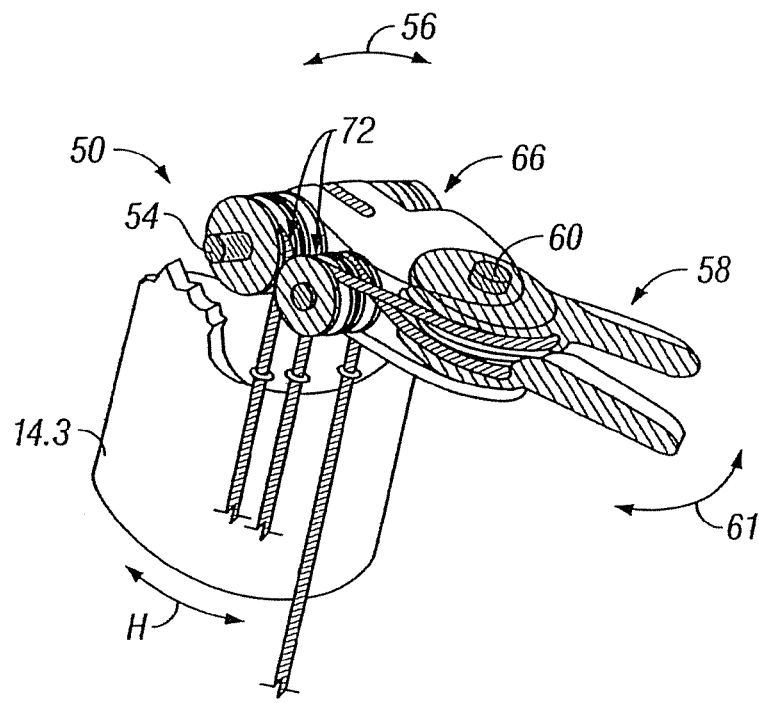
FIG. 8 is a perspective view of the wrist mechanism of FIG. 5 schematically illustrating the singularity at the 90° pitch position.

When the end effector 58 is oriented forward, the roll, pitch, and yaw provide rotational movements relative to three generally perpendicular axes. FIG. 8 shows the position of the end effector 58 after rotation in pitch in the direction 56 of the wrist member 52 around the pivotal connection 54 by about 90°. In this position, the yaw in the direction 61 around the pivotal connection 60 overlaps with the roll H of the working end 14.3. The overlap or redundancy results in the loss of one degree of freedom of movement of the end effector 58 at or near this position of singularity. In some applications, the end effector 58 may be used primarily at this position of about 90° pitch. It is desirable to provide a wrist mechanism that does not operate at a singularity in this position.

Roll-Pitch-Roll Mechanism

Figure 11:
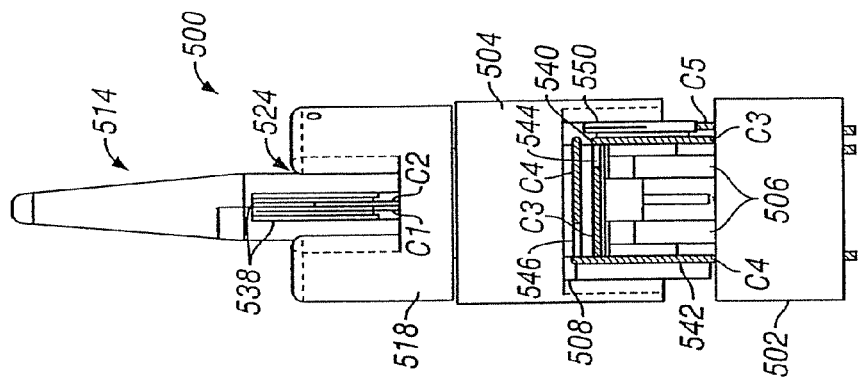
FIG. 11 is a side view of the wrist mechanism of FIG. 9 along arrow XI.
Figure 10:
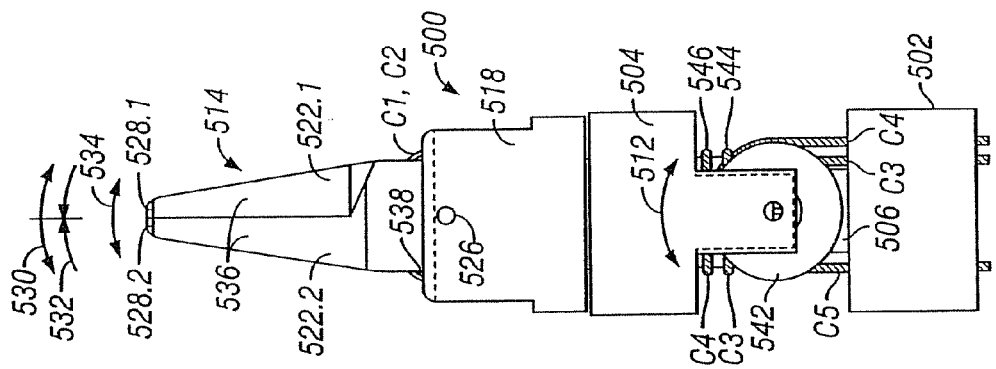
FIG. 10 is a front view of the wrist mechanism of FIG. 9 along arrow X.
Figure 9:
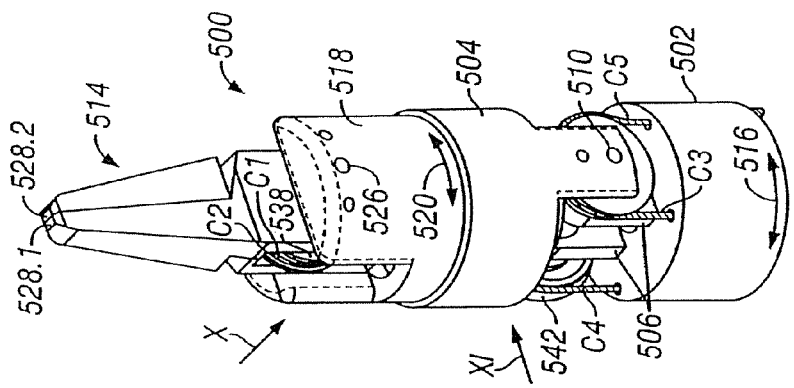
FIG. 9 is a perspective view of a roll-pitch-roll wrist mechanism according to a preferred embodiment of the present invention.

FIGS. 9-11 show a roll-pitch-roll wrist-like mechanism 500. In FIG. 9, the working end of the tool shaft is indicated at 502, and includes a pair of extensions 506. The wrist-like mechanism 500 includes a rigid wrist member 504. One end portion of the wrist member 504 forms a clevis 508 in which the extensions 506 of the working end 502 of the tool shaft are pivotally mounted by means of a pivotal connection 510. As best seen in FIG. 10, the wrist member 504 can pitch in the direction of arrows 512 about the pivotal connection 510. This rotation around the pivotal connection 510 in the direction 512 is referred to as the pivot or pitch of the wrist member 504. The end 502 is rotatable with the tool shaft around the shaft axis in the direction 516. This rotation around the shaft axis in the direction 516 is referred to as the roll of the working end 502.

An end effector, generally indicated by reference numeral 514, is supported on an end effector support base 518 which is pivotally mounted on an opposed end of the wrist member 504 to rotate around its axis in the direction 520 as shown in FIG. 9. In the embodiment shown, the axis of the base 518 coincides with the axis of the wrist member 504. The rotation in the direction 520 is referred to the distal roll of the end effector 514. This distal roll of the end effector 514 in the direction 520 is differentiated from the proximal roll of the working end 502 in the direction 516. In the position of the wrist mechanism 500 as shown in FIGS. 9-11, the distal roll 520 of the end effector 514 overlaps with the proximal roll 516 of the working end 502. Because the rotation of the wrist member 504 around the pivotal connection 510 provides pitch 512 of the end effector 514, the distal roll 520 generally will not coincide with the proximal roll 516. The wrist mechanism 500 as illustrated in FIGS. 9-11 is referred to as a roll-pitch-roll mechanism.

The end effector 514 is in the form of forceps or graspers for grasping tissue or the like during a surgical procedure. Accordingly, the end effector 514 has two parts 522.1, 522.2 together defining a jaw-like arrangement. The two parts 522.1, 522.2 are pivotally mounted in a clevis 524 on the base 518, by means of a pivotal connection 526. Free ends 528.1, 528.2 of the parts 522.1, 522.2 are angularly displaceable about the pivotal connection 526 toward and away from each other as indicated by arrows 530, 532 in FIG. 10. This movement is referred to as the grip of the end effector 514. The members 522.1, 522.2 can be displaced angularly about the pivotal connection 526 to change the orientation of the end effector 514 as a whole, relative to the wrist member 504. Thus, each part 522.1, 522.2 is angularly displaceable about the pivotal connection 526 independently of the other, so that the end effector 514 is, as a whole, angularly displaceable about the pivotal connection 526 in the direction 534, as shown in FIG. 10. This rotation around the pivotal connection 526 is referred to the yaw of the end effector 514. In the position of the wrist mechanism 500 as shown in FIGS. 9-11, the yaw 534 of the end effector 514 overlaps with the pitch 512 of the wrist member 504. Because the rotation of the base 518 provides distal roll 520 of the end effector 514, the yaw 534 generally will not coincide with the pitch 512. With the additional degree of freedom in yaw in the specific embodiment shown, the wrist mechanism 500 as illustrated in FIGS. 9-11 may be referred to as a roll-pitch-roll-yaw mechanism.

The parts 522.1, 522.2 each include an elongate finger portion or end effector element 536 and an end effector mounting formation in the form of, e.g., a pulley portion 538. The finger portion 536 may be integrally formed with the pulley portion 538. The pulley portion 538 defines a circumferentially extending channel for receiving an activation cable in a manner similar to the pulley portion 58.5 in the end effector 58 of FIGS. 5-7. Two elongate members such as cables C1, C2 are used to effect movement of the parts 522.1, 522.2 in yaw 534 and grip 530, 532. The cables C1, C2 pass from the wrist mechanism 500 internally through the shaft toward the housing 53 (FIG. 3). For simplicity, details of the pulley portion 538 in the end effector 514 of FIGS. 9-11 are omitted. The configuration and operation of the parts 522.1, 522.2 are similar to those of the parts 58.1, 58.2 in FIGS. 5-7.

In an alternate embodiment, the end effector 514 does not include the additional degree of freedom in yaw 534 but is still configured to perform the grip function. The parts 522.1, 522.2 perform gripping and does not move as a whole in yaw. For example, one part 522.1 may be substantially fixed with respect to the support base 518, while the other part 522.2 is rotatable relative to the pivotal connection 526 to move away from and toward the fixed part 522.1 in grip 530, 532. In that case, only one cable C2 is needed to manipulate the part 522.2 to effect the grip movement thereof (C1 is no longer needed). This alternate roll-pitch-roll mechanism with grip capability is simpler in structure and operation than the roll-pitch-roll-yaw mechanism with grip.

As best seen in FIG. 11, the pair of working end extensions 506 are flanked by two pulleys 540, 542 which are, coaxially positioned on the pivotal connection 510 and in the clevis 508 at the proximal end of the wrist member 504. A tangent pulley 544 which is associated with the pulley 540 is attached to the bottom of the end effector support base 518. Another tangent pulley 546 which is associated with the pulley 542 is also attached to the bottom of the base 518. The tangent pulleys 544, 546 in the specific embodiment shown are generally perpendicular to the pair of pulleys 540, 542, and move together with the base 518. The circumference of each tangent pulley 544 or 546 is in close proximity to the circumference of its associated pulley 540 or 542. In a specific embodiment, the tangent pulleys are integrally formed with the bottom of the base 518.

Two elongate elements such as cables C3, C4 are used to effect movement of the end effector 514 and support base 518 in distal roll 520. As best seen in FIG. 11, two cables C3, C4 are anchored on the tangent pulleys 544, 546, respectively, to effect distal roll 520 of the base 518 attached to the tangent pulleys 544, 546. Cable C3 wraps around a portion of the tangent pulley 544, rides over the pulley 540 and extends through the shaft 14.1 to the housing 53, while cable C4 wraps around a portion of the tangent pulley 546, rides over the pulley 542 and extends through the shaft 14.1 to the housing 53 (FIG. 3). The circumference of each tangent pulley 544 or 546 is in sufficiently close proximity to the circumference of its associated pulley 540 or 542 to allow the corresponding cable C3 or C4 to slide in the pulley channels securely through the approximately 90° change in orientation from one pulley to the other. In a preferred embodiment, cables C3, C4 are connected in the housing 53 and form a single cable. The single cable substantially does not change in length during distal roll 520 so that no tensioning spring or similar member is needed.

Another pulley 550 is disposed adjacent the pulley 540 and is coaxially positioned with the pulleys 540, 542 on the pivotal connection 510 and in the clevis 508 at the proximal end of the wrist member 504. An elongate element such as cable C5 is used to effect movement of the wrist member 504 in pitch 512. As seen in FIGS. 9-11, cable C5 is anchored on the pulley 550, rides over the pulley 540, and extends through the shaft 14.1 to the housing 53 (FIG. 3). In an alternate embodiment, another pulley is coaxially positioned adjacent the pulley 542 opposite from the pulley 550 on the other side of the pair of working end extensions 506, and the opposite end of cable C5 is anchored on that pulley. In the alternate embodiment, cable C5 substantially does not change in length during pitch 512 of the wrist member 504 so that no tensioning spring or similar member is needed.

Figure 12:
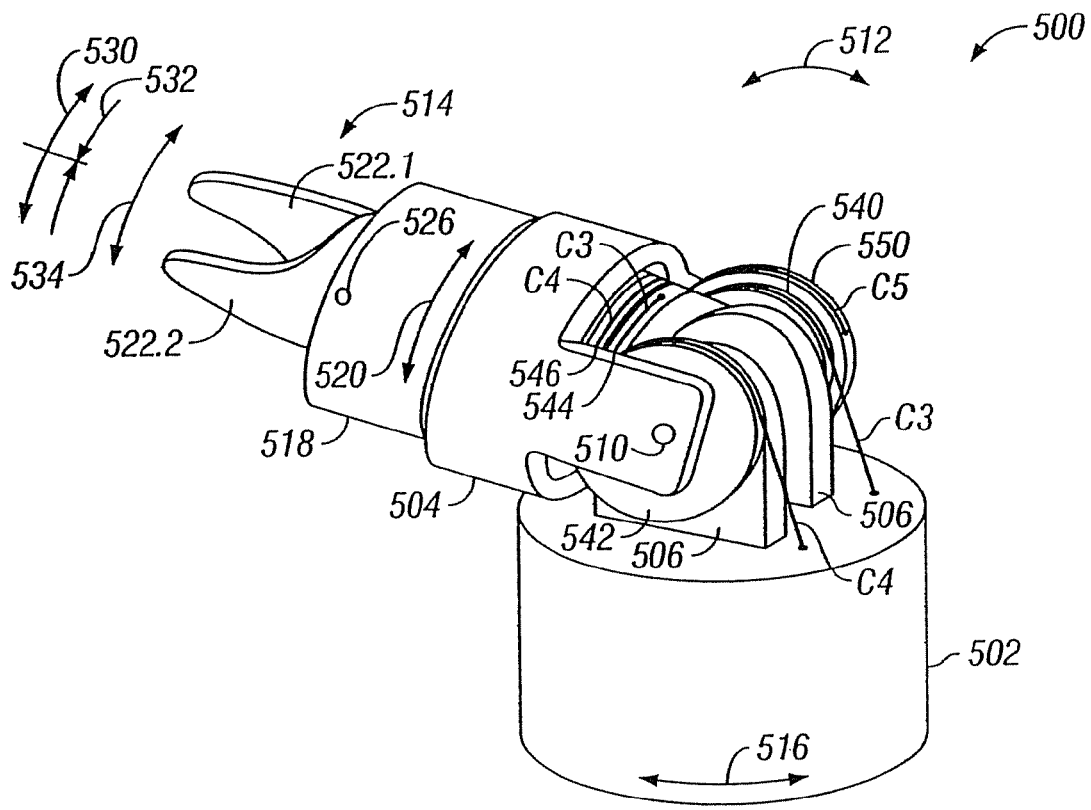
FIG. 12 is a perspective view of the wrist mechanism of FIG. 9 at the 90° pitch position.

FIG. 12 shows the position of the end effector 514 after rotation in pitch 512 of the wrist member 504 around the pivotal connection 510 by about 90°. In this position, there is no overlap among the proximal roll 516, pitch 512, and distal roll 520, which are oriented around axes that are generally perpendicular to each other, making the wrist mechanism 500 more suitable to operate in the 90° pitch position than the wrist mechanism 50 of FIGS. 5-8. In addition, the two parts 522.1, 522.2 of the end effector 514 are movable in yaw 524 and in grip 530, 532 in the specific embodiment shown. In the forward position of the end effector 514 as shown in FIGS. 9-11, the distal roll 520 coincides with the proximal roll 516, which presents a singularity. The addition of the yaw 524 of the end effector 514 in conjunction with the distal roll 520 in a preferred embodiment essentially eliminates the singularity by providing roll 516, pitch 512, and yaw 534 oriented around axes that are nonparallel and may be generally perpendicular to each other.

Bend Back Roll-Pitch-Roll Mechanism

Figure 13:
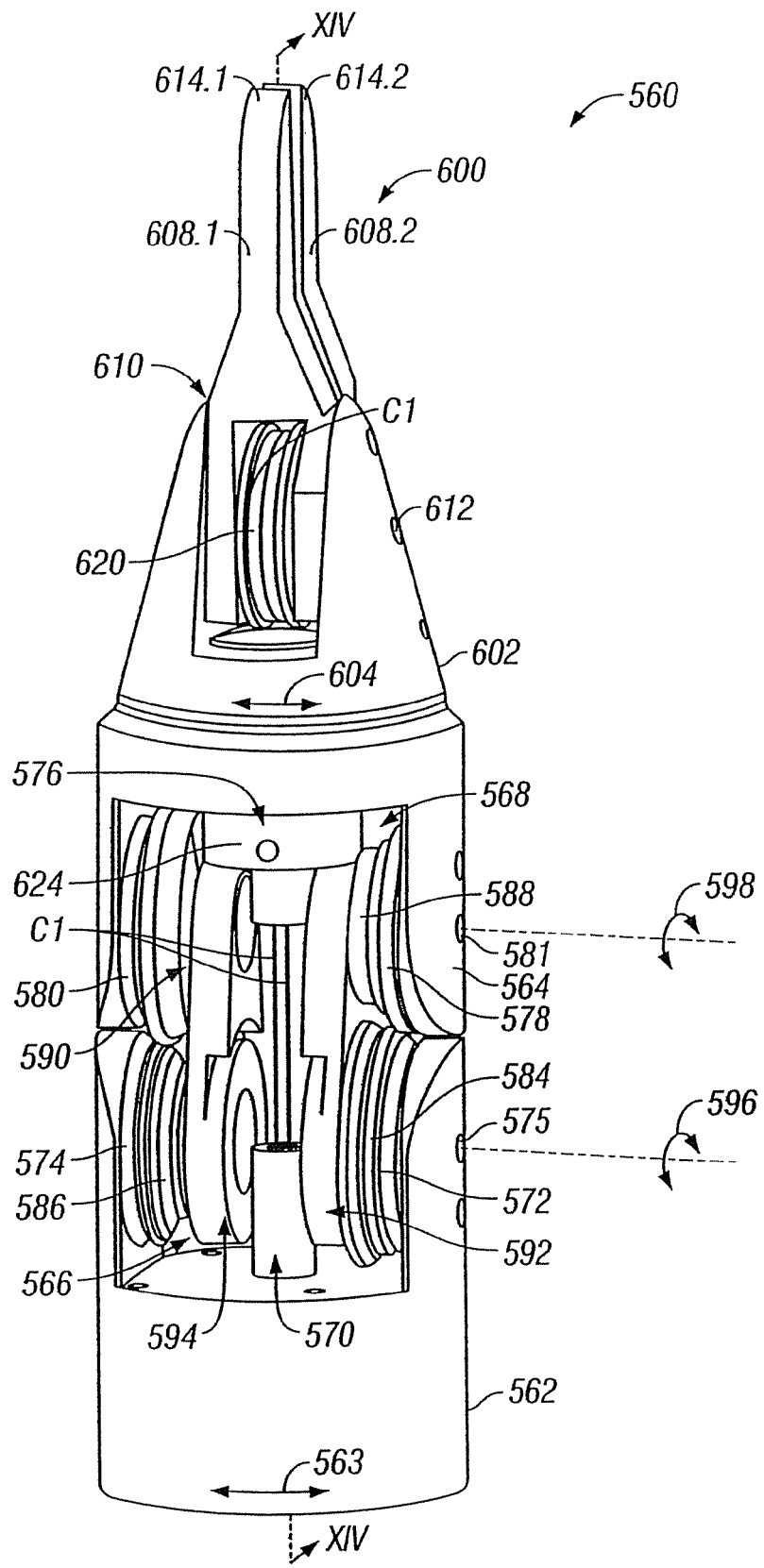
FIG. 13 is a perspective view of a roll-pitch-roll wrist mechanism according to another preferred embodiment of the present invention.

FIGS. 13-17 show a roll-pitch-roll wrist-like mechanism 560 including a bend back feature in the pitch direction to increase the versatility of the mechanism 560. In FIG. 13, the working end of the tool shaft is indicated at 562. The end 562 is rotatable with the tool shaft around the shaft axis in the proximal roll 563. The wrist-like mechanism 560 includes a rigid wrist member 564. The working end 562 forms a working end clevis 566, and one end portion of the wrist member 564 forms a wrist member clevis 568 facing the clevis 566. The working end 562 includes a central extension 570. Disposed in the working end clevis 566 are a first pair of pitch or knee pulleys 572, 574 on opposite sides of the central extension 570. The pulleys 572, 574 are coaxially positioned on a pivotal connection 575. A central extension 576 is located in the wrist member clevis 568. Disposed in the wrist member clevis 568 are a second pair of pitch or knee pulleys 578, 580 on opposite sides of the central extension 576. The pulleys 578, 580 are coaxially positioned on a pivotal connection 581. The second pair of pitch pulleys 578, 580 in the wrist member clevis 568 are coplanar with the first pair of pitch pulleys 572, 574 in the working end clevis 566, respectively.

Figure 14:
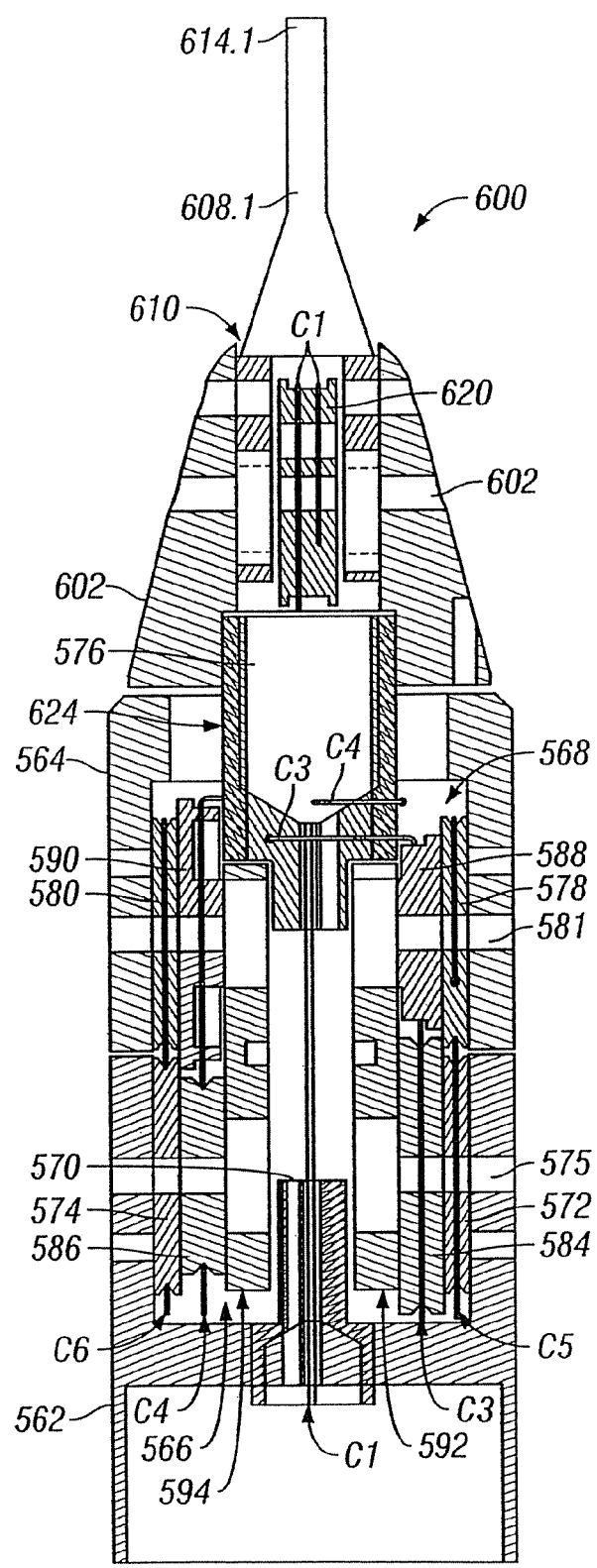
FIG. 14 is a sectional view of the wrist mechanism of FIG. 13 along XIV-XIV.

As best seen in FIGS. 13 and 14, a first pair of distal roll pulleys 584, 586 are disposed in the working end clevis 566, on opposite sides of the central extension 570. The pulleys 584, 586 are coaxially positioned on the pivotal connection 575. A second pair of distal roll pulleys 588, 590 are disposed in the wrist member clevis 568 on opposite sides of the central extension 576. The pulleys 588, 590 are coaxially positioned on the pivotal connection 581. The second pair of distal roll pulleys 588, 590 in the wrist member clevis 568 are coplanar with the first pair of distal roll pulleys 584, 586 in the working end clevis 566, respectively.

A pair of bend back pulley arms or lining arms 592, 594 extend between the working end clevis 566 and the wrist member clevis 568, and are disposed on opposite sides of the central extensions 570, 576. Each pulley arm 592, 594 has an end coaxially positioned on the pivotal connection 575 of the working end 562 and another end coaxially positioned on the pivotal connection 581 of the wrist member 564. Rotation of the bend back pulley arms 592, 594 relative to the working end 562 around the pivotal connection 575 in the direction 596 provides proximal pitch, while rotation of the wrist member 564 relative to the bend back pulley arms 592, 594 around the pivotal connection 581 in the direction 598 provides distal pitch. The proximal pitch 596 and distal pitch 598 allow the wrist member 564 to be bent back in pitch by more than 90° as discussed in more detail below.

The central extension 576 in the wrist member clevis 568 is connected to a support base 602 for an end effector, generally indicated by reference numeral 600. The central extension 576 may be integrally formed with the base 602. The support base 602 is pivotally mounted on an opposed end of the wrist member 564 to rotate around its axis in the direction 604, as shown in FIG. 13. In the embodiment shown, the axis of the base 602 coincides with the wrist axis of the wrist member 564. The rotation in the direction 604 is referred to the distal roll of the end effector 600. This distal roll of the end effector 600 in the direction 604 is differentiated from the proximal roll of the working end 562 in the direction 563. In the position of the wrist mechanism 560 as shown in FIGS. 13-16, the distal roll 604; of the end effector 600 coincides with the proximal roll 563 of the working end 562. Because the rotation of the wrist member 564 around the pivotal connections 575, 581 provides compound pitch 596, 598 of the end effector 600, the distal roll 604 generally will not coincide with the proximal roll 563. The wrist mechanism 560 as illustrated in FIGS. 13-17 is referred to as a bend back roll-pitch-roll mechanism.

The end effector 600 is in the form of forceps or graspers for grasping tissue or the like during a surgical procedure. Accordingly, the end effector 600 has two parts 608.1, 608.2 together defining a jaw-like arrangement. The two parts 608.1, 608.2 are pivotally mounted in a clevis 610 on the base 602, by means of a pivotal connection 612. Although free ends 614.1, 614.2 of the parts 608.1, 608.2 may be angularly displaceable about the pivotal connection 612 toward and away from each other in some embodiments, the specific embodiment shown in FIGS. 13-17 permits rotation of only the part 608.2 relative to the pivotal connection 612. The other part 608.1 is fixed relative to the base 602. The movable part 608.2 is movable toward and away from the fixed part 608.1 as indicated by arrows 616, 618 in FIG. 16. This movement is referred to as the grip of the end effector 600.

The movable part 608.2 includes a mounting formation in the form of, e.g., a pulley portion 620. The pulley portion 620 defines a circumferentially extending channel for receiving an elongate member such as an activation cable C1 which is anchored to the pulley portion 620, as best seen in FIGS. 13 and 14. The cable C1 pass through the central extensions 576, 570 and the shaft toward the housing 53 (FIG. 3). In a preferred embodiment, the cable C1 forms a continuous loop between the pulley portion 620 and the housing 53 and does not change in length during grip 616, 618 of the end effector 600, so that no tensioning spring is needed.

Two elongate elements such as cables C3, C4 are used to effect movement of the end effector 600 and support base 602 in distal roll 604. As best seen in FIG. 14, two cables C3, C4 are anchored on the tangent surface 624 of the central extension 576 of the base 602 to effect distal roll 604 of the base 602 (FIG. 13). Cable C3 wraps around a portion of the tangent surface 624, while cable C4 wraps around another portion of the tangent surface 624. Cable C3 rides over the roll pulleys 588, 584 and extends through the shaft 14.1 to the housing 53, while cable C4 rides over the roll pulleys 590, 586 and extends through the shaft 14.1 to the housing 53 (FIG. 3). The circumference of the tangent surface 624 is in sufficiently close proximity to the circumferences of the two roll pulleys 588, 590 to allow the corresponding cables C3, C4, respectively, to slide in the pulley channels securely through the approximately 90° change in orientation from the roll pulleys 588, 590 to the tangent surface 624. In a preferred embodiment, cables C3, C4 are connected in the housing 53 and form a single cable. The single cable substantially does not change in length during distal roll 604 so that no tensioning spring or similar member is needed. For clarity, cables C3, C4 are not shown in FIGS. 13 and 15-17. In an alternate embodiment, the tangent surface 624 may include a pair of circumferential channels for receiving the cables C3, C4 such as those for the tangent pulleys 544, 546 shown in FIG. 11 for the wrist mechanism 500.

As best seen in FIG. 14, two cables C5, C6 are provided for activating roll 596, 598 of the wrist member 564. Cable C5 is anchored on the pulley 578, rides over the pulleys 578, 572, and extends through the shaft 14.1 to the housing 53 (FIG. 3). Cable C6 is anchored on the pulley 580, rides over the pulleys 580, 574, and extends through the shaft 14.1 to the housing 53. In a preferred embodiment, the two cables C5, C6 are connected to form a single cable that substantially does not change in length during pitch 596, 598 of the wrist member 564 so that no tensioning spring is needed.

FIG. 17 illustrates the bend back feature of the wrist mechanism 560. The compound pitch 596, 598 around pivotal connections 575, 581 allows the wrist member 564 and end effector 600 to bend back by an angle θ of more than about 90° from the forward position of FIGS. 13-16, desirably by more than about 120°, and more desirably by more than about 135°. Thus, the angle between the shaft axis and the wrist axis is about 180° when the end effector 600 is in the forward position, and is less than 90° in the bent back position, and may be down to less than about 60° or less than about 45°. The ability to bend back the end effector 600 renders the wrist mechanism 560 more versatile and adaptable to accessing hard to reach locations, particularly with small entry points such as those involving spinal, neural, or rectal surgical sites. The use of the linking arms 592, 594 provides this capability while maintaining the size of the tool 560 to a sufficiently small size for minimally invasive surgical applications.

The above-described arrangements of apparatus and methods are merely illustrative of applications of the principles of this invention and many other embodiments and modifications may be made without departing from the spirit and scope of the invention as defined in the claims. For instance, the linking arms may have other configurations. Different actuation mechanisms other than activating cables may be used to manipulate the wrist member and end effector. The scope of the invention should, therefore, be determined not with reference to the above description, but instead should be determined with reference to the appended claims along with their full scope of equivalents.

What is claimed is:

1. An articulated surgical instrument for minimally invasive surgery comprising:
   a tool shaft having a proximal end and a working end;
   a wrist member having a proximal end and a distal end, the proximal end of the wrist member coupled to the working end of the tool shaft by a pivotal connection defining a pitch axis;
   a base coupled to the distal end of the wrist member, the base supporting an end effector;
   first and second pulleys coaxially positioned on the pitch axis;
   first and second tangent surfaces attached to the bottom of the base, the first and second tangent surfaces each rotatable about a distal roll axis perpendicular to and intersecting the pitch axis;
   a first elongate element engaging the first tangent surface and the first pulley, the first elongate element running through the tool shaft; and
   a second elongate element engaging the second tangent surface and the second pulley, the second elongate element running through the tool shaft;
   the instrument further comprising a pitch pulley coaxially positioned on the pitch axis, and a pitch elongate element engaging the pitch pulley, the pitch elongate element running through the wrist member through the tool shaft.

2. The instrument of claim 1, the end effector further comprising first and second parts pivotally mounted on the base by a pivotal connection defining a yaw axis.

3. The instrument of claim 2, the first and second parts each comprising a pulley portion mounted coaxially on the pivotal connection defining the yaw axis, the instrument further comprising a third and fourth elongate element coupled with the pulley portions of the first and second parts, respectively, the third and fourth elongate elements running through the wrist member through the tool shaft.

4. The instrument of claim 3, the first, second, third, fourth, and pitch elongate elements running through the tool shaft and coupled to first, second, third, fourth, and pitch actuators, respectively, the actuators disposed adjacent the proximal end of the tool shaft.

5. The instrument of claim 1, the first and second elongate elements running through the tool shaft and coupled to first and second actuators, respectively, the actuators disposed adjacent the proximal end of the tool shaft.

6. The instrument of claim 1, the first, second, and pitch elongate elements running through the tool shaft and coupled to first, second, and pitch actuators, respectively, the actuators disposed adjacent the proximal end of the tool shaft.

7. The instrument of claim 1, the first and second tangent surfaces being portions of a single tangent pulley.

8. The instrument of claim 1, the first tangent surface being a first tangent pulley, and the second tangent surface being a second tangent pulley.

9. The instrument of claim 1, the proximal portion of the wrist member comprising a clevis, the working end of the tool shaft comprising an extension, the pivotal connection contacting the clevis and the extension.

\* \* \* \* \*